United States Patent [19]
Desch

[11] Patent Number: 5,251,616
[45] Date of Patent: Oct. 12, 1993

[54] ADJUSTABLE TRACHEOSTOMY TUBE ASSEMBLY

[75] Inventor: Larry W. Desch, Madison, Wis.

[73] Assignee: Wisconsin Alumni Research Foundation, Madison, Wis.

[21] Appl. No.: 918,179

[22] Filed: Jul. 23, 1992

[51] Int. Cl.[5] ............................................. A61M 16/00
[52] U.S. Cl. ..................... 128/200.26; 128/207.14; 128/207.17; 128/912; 128/DIG. 26
[58] Field of Search ..................... 128/200.26, 207.14, 128/207.15, 207.17, 912, DIG. 26

[56] References Cited

U.S. PATENT DOCUMENTS

| | | | |
|---|---|---|---|
| 2,923,299 | 2/1960 | Blackwood | 128/207.17 |
| 3,499,450 | 3/1970 | Rathjen | 128/207.17 |
| 3,688,774 | 9/1972 | Akiyama | 128/200.26 |
| 3,987,798 | 10/1976 | McGinnis | 128/DIG. 26 |
| 4,235,229 | 11/1980 | Ranford et al. | 128/207.17 |
| 4,304,228 | 12/1981 | Depel | 128/207.17 |
| 4,332,245 | 6/1982 | Boone, Sr. | 128/207.17 |
| 4,527,559 | 7/1985 | Roxburg et al. | 128/207.17 |
| 4,658,813 | 4/1987 | Jones | 128/207.14 |
| 4,668,222 | 5/1987 | Poirier | 128/DIG. 26 |
| 4,683,882 | 8/1987 | Mischinski | 128/DIG. 26 |
| 4,817,598 | 4/1989 | LaBombard | 128/207.14 |
| 4,909,248 | 3/1990 | McLennan-Anderson | 128/207.14 |
| 5,026,352 | 6/1991 | Anderson | 128/207.17 |
| 5,054,482 | 10/1991 | Bales | 128/207.14 |
| 5,067,496 | 11/1991 | Eisele | 128/207.15 |
| 5,069,206 | 12/1991 | Crosbie | 128/207.17 |
| 5,123,410 | 6/1992 | Greene et al. | 128/207.17 |
| 5,146,913 | 9/1992 | Khorsandian et al. | 128/DIG. 26 |

Primary Examiner—Edgar S. Burr
Assistant Examiner—Aaron J. Lewis
Attorney, Agent, or Firm—Ross & Stevens

[57] ABSTRACT

A tracheostomy tube assembly, particularly for pediatric use, is provided. The tracheostomy tube assembly includes a tracheostomy tube having an adjustable length and being adapted for insertion into the trachea through an opening in a patient's neck. The assembly further includes a neck collar adapted to fit on the exterior of the patient's neck. The neck collar has an opening through which the tracheostomy tube passes. The neck collar includes a locking means adapted to adjustable maintain the tracheostomy tube at a predetermined length in the trachea.

9 Claims, 4 Drawing Sheets

ADJUSTABLE TRACHEOSTOMY TUBE ASSEMBLY

FIELD OF THE INVENTION

The present invention is directed to a tracheostomy tube assembly. The invention is specifically directed to an adjustable tracheostomy tube assembly sized for use in infants, children and adults. The tracheostomy tube assembly may be used for disorders such as bronchopulmonary dysplasia, pulmonary diseases or central apnea.

BACKGROUND OF THE INVENTION

A tracheostomy is a surgical procedure performed on a patient when there is a blockage in the natural airways of a patient's throat, which blockage causes difficulty in breathing. An incision is made in the patient's throat, and a tracheostomy tube or cannula is inserted through the incision into the trachea. The procedure allows air to bypass the nose and throat and pass into the trachea in the respiratory process.

Tracheostomy tubes are well-known in the art, especially for adult patients. For example, U.S. Pat. No. 4,235,229 to Ranford et al. is directed to an adjustable tracheostomy tube assembly, which includes three prominent features: the tracheostomy tube, a neck collar, and a tube extension. The tracheostomy tube includes a ridged section at the proximal end, i.e., the patient's neck end. The collar includes a sleeve portion, which has lugs or tabs designed to interact with the ridges in the tracheal tube. In this manner, the tracheostomy tube can be manipulated back and forth through the sleeve portion to lengthen or shorten the tube in the trachea as required for the individual patient. The lugs connect the tube in position.

Some prior art disclosures relating to tracheostomy tubes suggest pediatric use. For example, U.S. Pat. No. 4,909,248 to McLennan-Anderson is directed to a tracheostomy tube assembly specifically meant for pediatric use. The tracheostomy tube assembly is designed to eliminate the risk of the tube becoming blocked at the patient's neck by folds of skin contacting the open end of the tube. U.S. Pat. No. 5,054,482 to Bales is directed to a tracheostomy tube assembly, described as being useful for neonates and infants. The assembly includes a tracheostomy tube connected to a base that matches the contour of the patient's neck. U.S. Pat. No. 3,499,450 to Rathjen is also directed to a pediatric-sized tracheostomy tube. The tube is manufactured to any suitable length and then cut to a desired length before insertion. The excess is then discarded. Thus, the tracheostomy tube is stocked in only one length.

One of the difficulties normally associated with performing a tracheostomy on an infant, adolescent, or smaller-sized patient (referred to hereinafter as a "child") is that the child does not have a fully developed neck. Because of this, a tracheostomy procedure normally associated with an adult cannot be efficiently conducted on a child. Further, because most tracheostomy tubes now used on adolescent children are essentially down-sized or manipulated versions of adult tracheostomy tube assemblies, they are ill-fitting and must be continually replaced. Additionally, the tracheostomy tubes are not adequately adapted to the angle of the trachea and the short necks of children. The importance of a well-fitting device, particularly in situations were apprehensive parents must tend to infants wearing the tracheostomy tube assembly, cannot be over-emphasized.

While tracheostomy tube assemblies are available for use in children, and specifically for pediatric use, there is no known adjustable tracheostomy tube assembly specifically designed to adapt to the specific needs of children and to allow for the improved care of the tracheostomy site.

SUMMARY OF THE INVENTION

One object of the present invention is to provide a tracheostomy tube assembly which is easy to manufacture. Another object is to provide a tracheostomy tube assembly which has an adjustable tracheostomy tube length to adapt to individual patient needs, and especially the needs of small patients and children.

In conforming with these and other objects, the present invention provides a tracheostomy tube assembly comprising a tracheostomy tube having an adjustable length. The tracheostomy tube has a first end adapted for insertion into the trachea through an incision in a patient's neck and a second end adapted to extend from the trachea. The tracheostomy tube may be provided with a predetermined "memory" curvature adapted to provide the proper bend or curve in the tube for insertion into the trachea. Alternatively, a tube guide, a generally rigid tube sleeve having a predetermined curvature, is provided with a directional channel for properly inserting the tube into the trachea.

The tracheostomy tube assembly further includes a neck collar adapted to fit on the exterior of the patient's neck. The neck collar has an opening through which the tracheostomy tube passes. If the tube guide is used, the tube guide is preferably connected to the neck collar such that the tracheostomy tube opening in the neck collar aligns with the channel in the tube guide.

The tracheostomy tube assembly is also provided with a locking means. The locking means is preferably secured to the neck collar and adapted to lock or maintain the tracheostomy tube at a predetermined length in the trachea. An important structural feature of the locking means is that it enables the length of the tracheostomy tube to be adjustable within the patient's trachea.

The present invention advantageously provides a tracheostomy tube assembly which may conveniently, easily and quickly adjust the length of the tracheostomy tube to conform to individual patient needs. In this manner, the tracheostomy tube assembly of the present invention improves the way in which newborns and young infants, especially those born premature, are managed with a tracheostomy. Thus, the same tracheostomy tube assembly may be used on a variety of patients having different neck sizes. For example, in an infant the tube can be "locked" to the neck collar by the locking means such that the distal end of the tube, that is the end entering the trachea, is very short, less than a few centimeters. The tube can be lengthened by feeding it through the neck collar and locked into place for larger patients. Additionally, with the contemplated locking means, the tube can easily be adjusted, i.e., lengthened or shortened on a daily or even hourly basis without requiring removal of the tube assembly.

Because of its component structure, the tube assembly can be provided with a number of different sized tracheostomy tubes, neck collars, locking means and guide tubes. For example, the length of the tracheostomy tube can be adjusted by loosening the locking means and pulling or pushing the tracheostomy tube as desired. Adjusting the length of the tracheostomy tube will prevent the distal end from maintaining its location at one spot in the patient's trachea. This can prevent any irritation or ulcers developing by the continuous rubbing of the distal end on one spot.

The tracheostomy tube can also be easily removed and replaced with a different tracheostomy tube without having to remove the entire tracheostomy tube assembly.

Further, the use of small diameter tubing helps to eliminate some of the dead space problem seen with the attachment of the tracheostomy tube to the large tubing for oxygen delivery or for a ventilator.

Further still, the fenestrated design of the neck collar, as well as the longer tracheostomy tube outside the trachea, allows for better exposure of the skin.

Other objects and advantages will become apparent to those skilled in the art by reading the following detailed description of the invention in connection with the accompanying drawings.

DETAILED DESCRIPTION OF THE INVENTION

Figure 1:
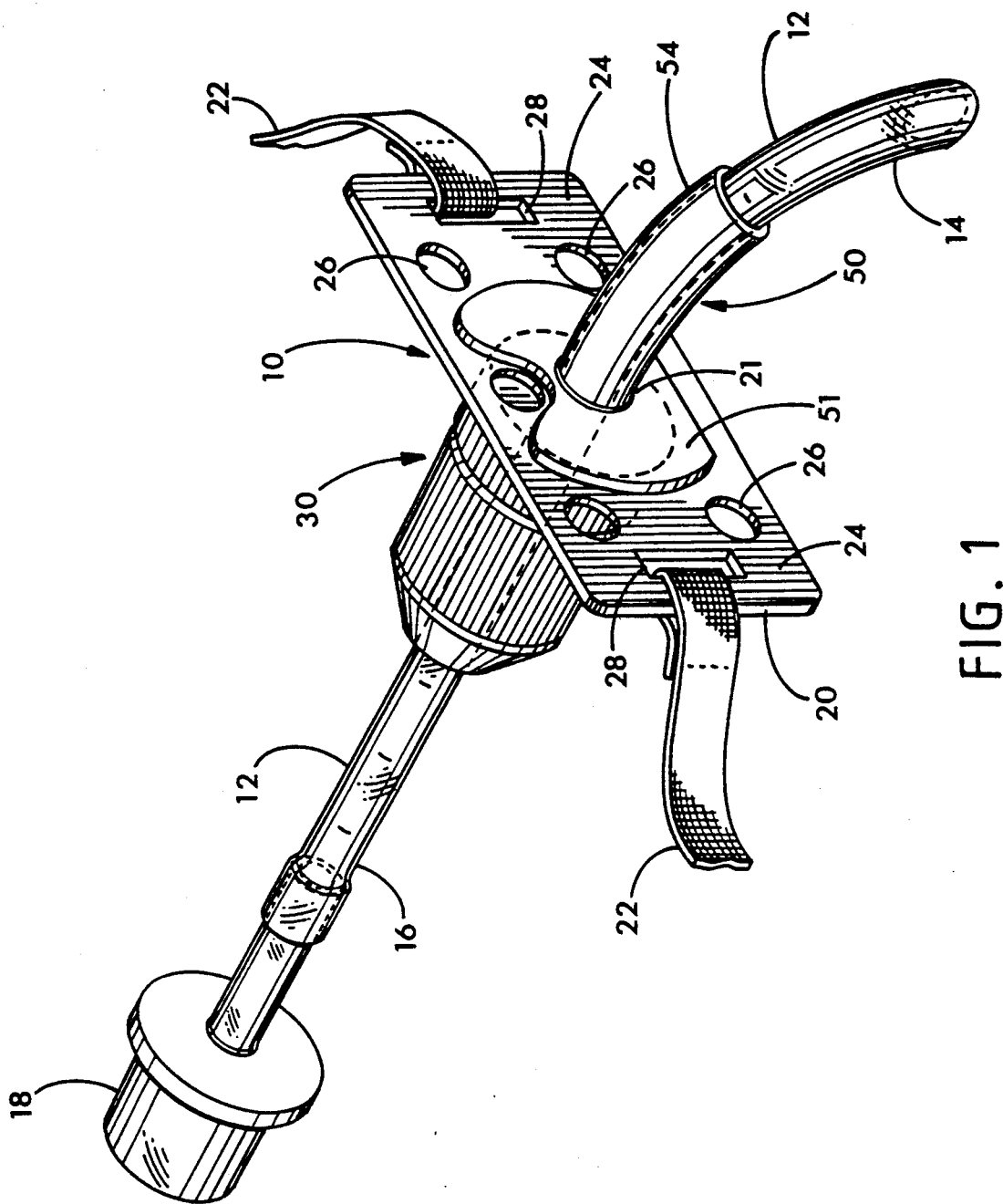
FIG. 1 is a perspective view showing the tracheostomy tube assembly of the present invention.

Referring now to the drawings wherein like reference numerals designate like or corresponding parts throughout the figures, FIG. 1 illustrates a tracheostomy tube assembly, referenced generally as 10. The assembly is designed to provide an air passageway through the neck of a patient when the natural air passageways in the patient's throat are blocked.

Tracheostomy tube

The assembly 10 includes a tracheostomy tube or cannula 12 having a distal end 14, which is designed to be inserted into the patient's neck, and a proximal end 16 extending out of the patient's neck and ending with a tubing connector 18. The tubing connector 18 is illustrated as a generic device representing a variety of connection elements for connecting the tracheostomy tube 12 to respiratory machines or the like.

Neck Collar

The tube 12 is positioned in the trachea and maintained on the neck by a neck collar 20. As illustrated in FIG. 1, the neck collar 20 is a flanged piece of flexible material, such as a molded plastic or a polypropylene, which may be adapted for mounting on the patient's neck. The neck collar 20 may be any size and shape which is suitable for use on a patient. Thus, while a rectangular neck collar 20 is illustrated, it is within the scope of the present invention to provide other suitable shapes.

The neck collar 20 includes a tube passageway 21 through which the tube 12 passes. The passageway 21 is generally centrally located on the neck collar 20 and bordered by two wings or flanges 24 on either side of the tracheostomy tube 12.

Preferably, the neck collar 20 is provided with a plurality of ventilation openings 26. The ventilation openings 26 allow air to circulate through the neck collar 20 to the patient's neck to assist in preventing skin rashes or other irritations, which may develop as the result of long term use of the assembly 10.

The neck collar 20 is secured to the patient's neck by neck straps 22 or the like in a manner known to the art. The straps 22 may be formed of any flexible material, such as woven cloth, string, tape or plastic. The straps 22 are attached to the neck collar 20 through slots 28 at each end of the neck collar.

Locking Means

The assembly 10 is also provided with a locking means 30. The locking means 30 maintains the tube 12 in place on the neck collar 20 at a predetermined, proper length for the tube 12 in the patient's trachea.

Figure 3:
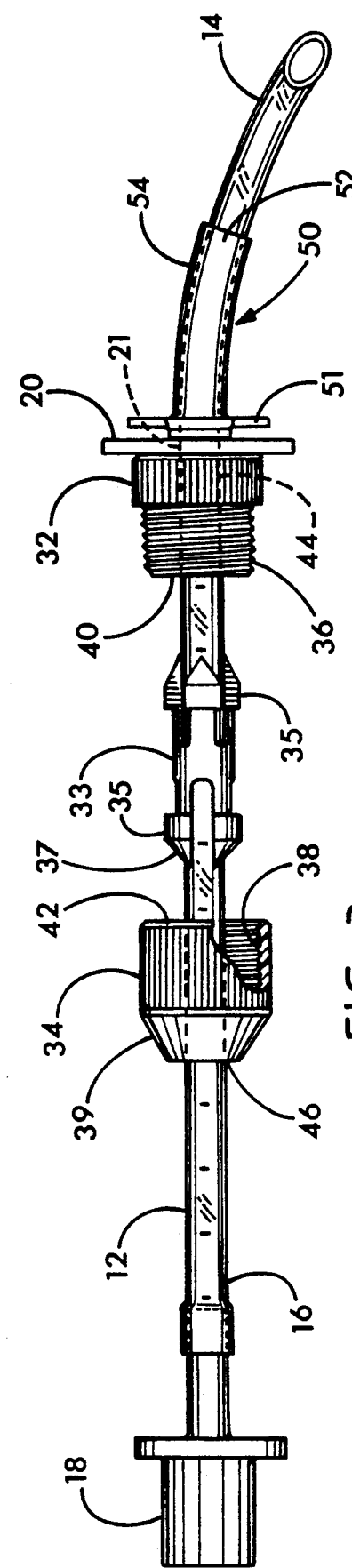
FIG. 3 is an exploded view of the assembly illustrated in FIG. 2.
Figure 4:
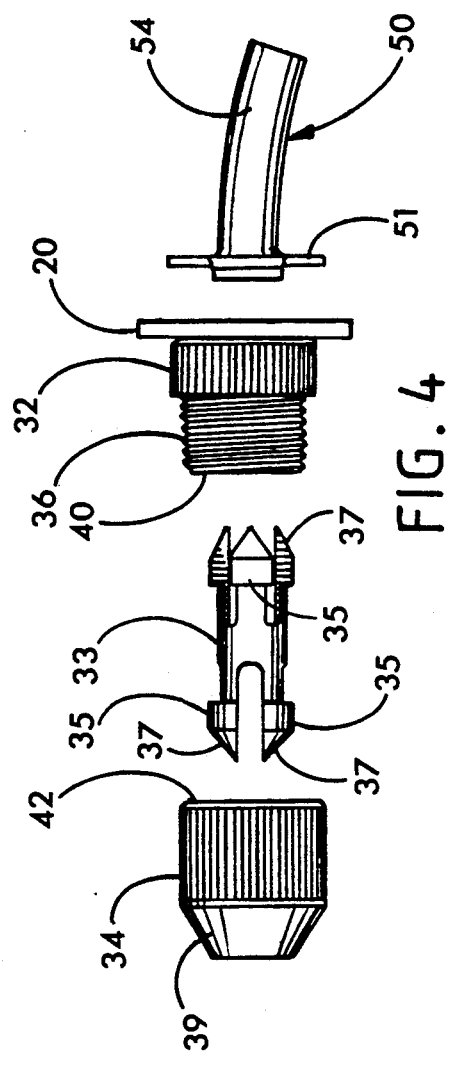
FIG. 4 is an exploded side view of an alternative embodiment of the assembly of the present invention.

As illustrated in FIGS. 3 and 4, a preferred locking means 30 is a three-part mating lock assembly having a locking base 32, affixed to the neck collar 20, a locking mate 34, which threadably attaches to the base 32, a friction member 33, a generally tubular structure encircling the tracheostomy tube 12 at the location define by the locking base 32 and the locking mate 34. The locking base 32 is provided with base threads 36, which coact with the mate threads 38 of the mate 34 to threadably position the mate 34 onto the base 32. The base 32 is provided with an axial base channel 40, which aligns with an axial mate channel 42 in the mate 34.

The friction member 33 is provided with a plurality of biasing elements 35 having tapered ends 37. The purpose of the friction member 33 is to lock the tube 12 by preventing the tube from sliding within the locking means 30 as the mate 34 is threadably mounted on the base 32. By tightening the mate 34 to the base 32, the tapered ends 37 of the biasing elements 35 are urged inward and against the tube 12 by the tapered shape of the locking means, illustrated at 39 on the locking mate 34. In this manner, the locking means 30 can be adjustably tightened onto the tracheostomy tube 12.

The locking means 30 therefore inhibits movement of the tube 12 in relationship to the neck collar 20. On the other hand, the locking means 30 is easily loosened to allow proper positioning and movement of the tracheostomy tube 12. For example, if the tube 12 in the trachea needs to be lengthened, the locking means 30 can be loosened as described above, and the tube 12 can simply be pushed into the trachea. Shortening the tracheostomy tube 12 can easily be accomplished by pulling the tube 12 from the loosened locking means 30.

Alternative Embodiment of the Tracheostomy Tube

Figure 5:
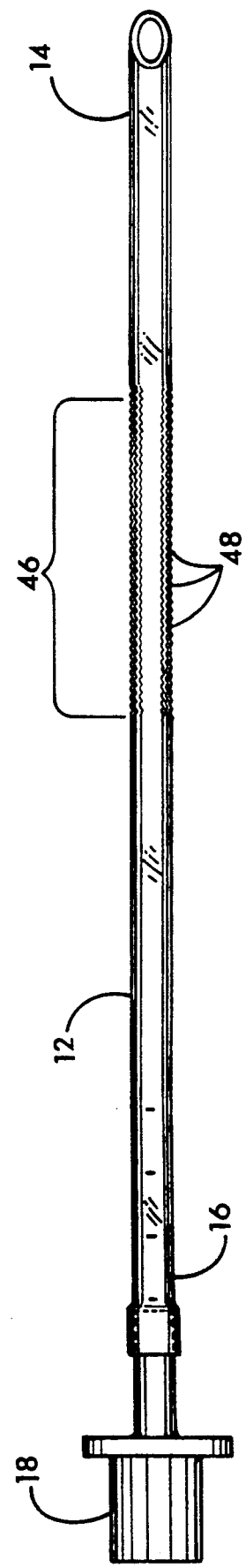
FIG. 5 is a side view in elevation of an alternative embodiment of the tracheostomy tube of the present invention.

Illustrated in FIG. 5 is another embodiment of the tracheostomy tube 12. Here, the tracheostomy tube 12 is provided with a texturized surface 46 in the form of ridges 48. The surface 46 is designed to further coact with the locking means 30 to more effectively eliminate any slippage of the tube 12 with respect to the locking means 30.

Guide Tube

Preferably, the tracheostomy tube assembly 10 of the present invention is provided with a guide tube 50, as illustrated in FIGS. 1-4. The guide tube 50 is affixed to the neck collar 20 as illustrated in FIGS. 1 and 3. The guide tube 50 is made of a short, relatively inflexible tube of metal or plastic. The guide tube 50 includes a base plate 51 for affixing the guide tube 50 to the neck collar 20, and a channel 52 which serves as an introducer or trocar for the tracheostomy tube 12 into the patient's trachea. It is within the scope of the present invention to provide a one-piece neck collar/guide tube unit, which may be extended or otherwise formed of plastic or other suitable materials.

As illustrated in FIGS. 1 and 3, the guide tube 50 is formed with a predetermined bend or angle, illustrated at 54, to form a proper downward directional guide for a tracheostomy tube 12 entering the trachea. Therefore, the tracheostomy tube 12 itself does not have to be specially formed to include a predetermined memory curve. The tracheostomy tube 12 can then be formed of standard straight, flexible tubing known to the art.

Assembling the Tracheostomy Tube Assembly

In a preferred mode, the locking base 32 of the locking means 30 is attached to the neck collar 20 at the area of the opening 21 in the neck collar 12 to form a one-piece structure as illustrated in FIG. 3. The guide tube 50 is attached at the other side of neck collar 20. In this manner, the channel 40 in the base 36, the tube passageway 21 in the neck collar 20, and the guide tube channel 52 in the guide tube 50 are aligned to form a continuous channel to direct the tracheostomy tube 12 into the trachea.

Figure 2:
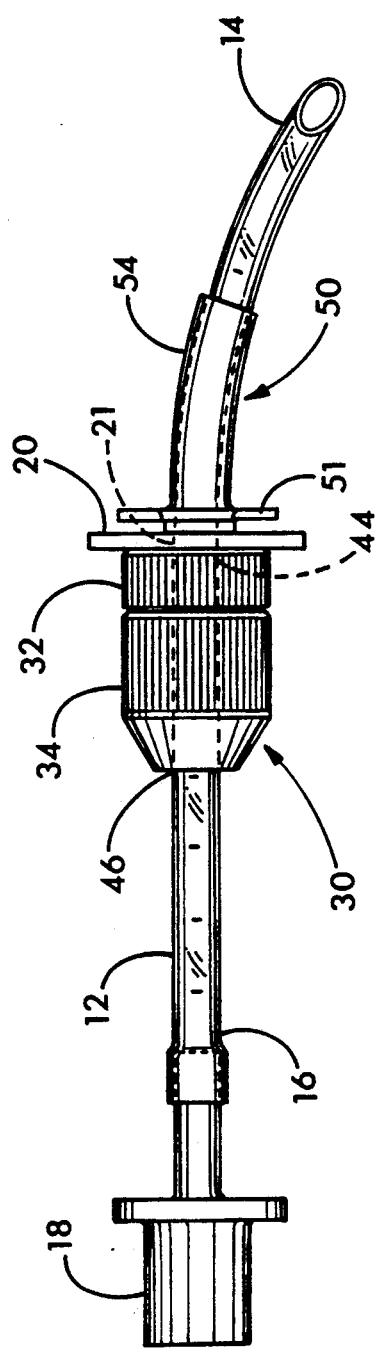
FIG. 2 is a side view in elevation of the assembly illustrated in FIG. 1.

To assemble the tracheostomy tube assembly 10, the locking mate 34 of the locking means 30 is loosened from the locking base 36 thereby allowing sufficient space for passing the tracheostomy tube 12 through the the channels 40, 42. The tracheostomy tube 12 is threaded through the channels 40, 42 and the opening 21 of neck collar 20. The locking mate 34 then threadably coacts with the locking base 32 as illustrated in FIG. 2. As the locking mate 34 is threadably attached to the locking base 32, the friction member 33 within the locking means 30 is activated to reduce the diameter of the channels 40, 42, which impedes the sliding movement of tracheostomy tube 12 through the opening 21 and channels 40 and 42. In this manner, the length of tracheostomy tube 12 entering the trachea can be customized.

Figure 6:
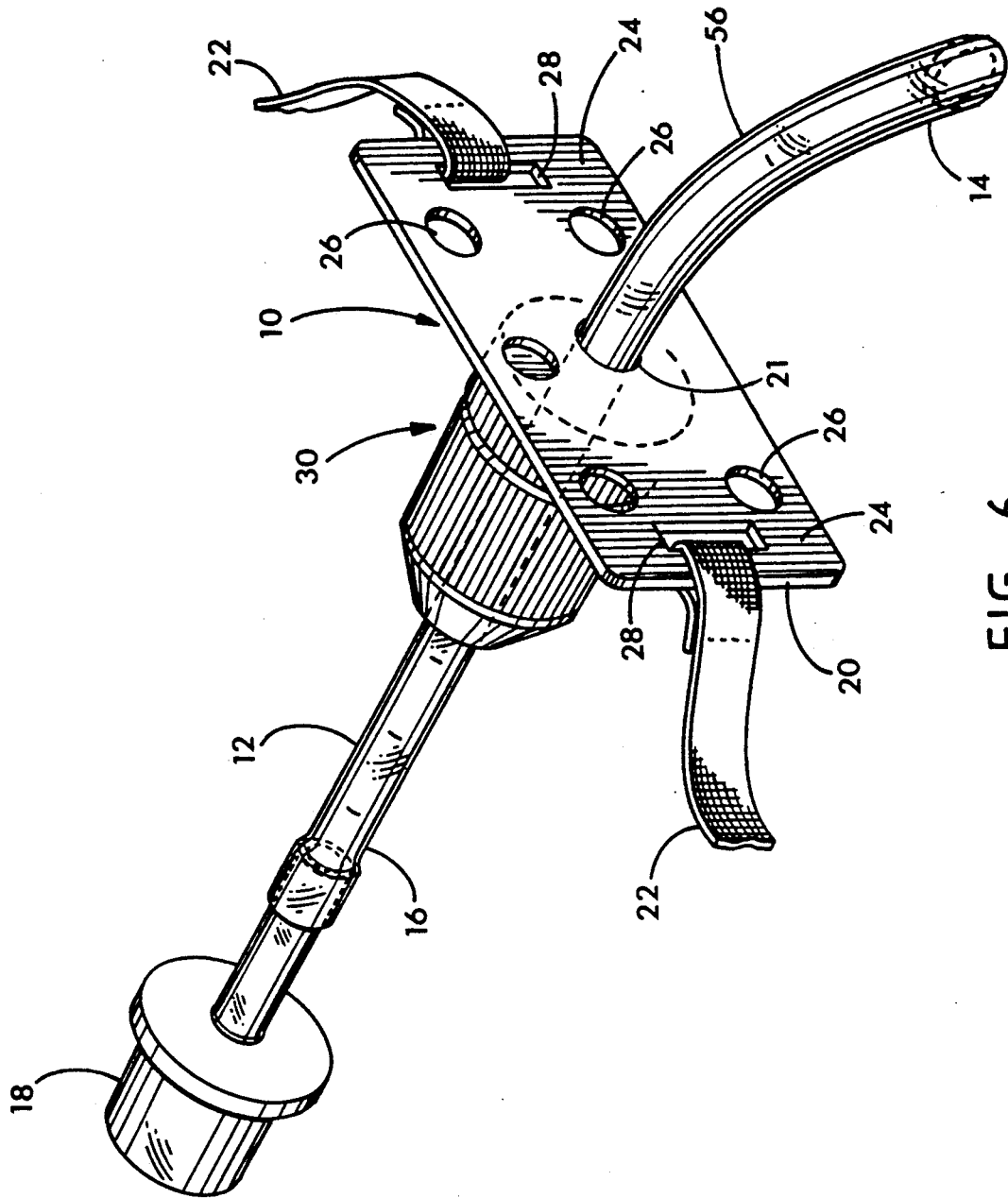
FIG. 6 is a perspective view of an alternative embodiment of the tracheostomy tube assembly of the present invention.

Alternatively, the tube assembly 10 of the present invention may be provided without a guide tube 50 as illustrated in FIG. 6. In this manner, the tracheostomy tube 12 includes a predetermined memory curve illustrated at 56 to adjust to the shape and design of the patient's trachea.

It is understood that the invention is not confined to the particular construction and arrangement herein illustrated and described, but embraces such modified forms thereof as come within the scope of the following claims.

What is claimed is:

1. A tracheostomy tube assembly comprising:
   a. a tracheostomy tube having an adjustable length, the tracheostomy tube having a first end adapted for insertion into the trachea through an incision in a patient's neck and a second end adapted to extend from the trachea;
   b. a neck collar adapted to fit on the exterior of the patient's neck, the neck collar having an opening through which the tracheostomy tube passes; and
   c. locking means secured to the neck collar and including means for allowing passageway of the tracheostomy tube therethrough, the locking means further including means independent of the neck collar and freely slidable along the tracheostomy tube in a loosened adjustment position for providing freely slidable release of the tracheostomy tube in said loosened adjustment position, said means independent of the neck collar for providing a secure friction gripping of the tracheostomy tube in a tightened position to secure the tracheostomy tube at a predetermined length.

2. The tracheostomy tube assembly of claim 1 further comprising a neck fastening means attached to the neck collar for holding the tracheostomy tube assembly in position.

3. The tracheostomy tube assembly of claim 1 wherein the tracheostomy tube has a predetermined curvature adapted for placing the tracheostomy tube in the trachea.

4. The tracheostomy tube assembly of claim 1 wherein the tracheostomy tube has a texture to suppress slippage between the tracheostomy tube and the locking means.

5. The tracheostomy tube assembly of claim 1 further comprising a guide tube of predetermined curvature adapted for insertion into the trachea and through which the tracheostomy tube is removably placed.

6. The tracheostomy tube assembly of claim 5 wherein the guide tube is affixed to the neck collar.

7. The tracheostomy tube assembly of claim 1 wherein the neck collar comprises a flexible material.

8. The tracheostomy tube of claim I wherein the neck collar comprises ventilating openings.

9. The tracheostomy tube of claim 1 wherein the locking means comprises a base member and mating member, wherein the base member is affixed to the neck collar.

* * * * *